United States Patent [19]

Alvarez

[11] Patent Number: 4,813,942

[45] Date of Patent: Mar. 21, 1989

[54] THREE STEP WOUND TREATMENT METHOD AND DRESSING THEREFOR

[75] Inventor: Oscar M. Alvarez, East Brunswick, N.J.

[73] Assignee: Bioderm, Inc., Plainsboro, N.J.

[21] Appl. No.: 26,950

[22] Filed: Mar. 17, 1987

[51] Int. Cl.$^4$ ............................................. A61M 35/00
[52] U.S. Cl. .................................... 604/290; 604/304; 128/156; 424/445; 424/448
[58] Field of Search ........ 128/156; 604/290, 304–308, 604/336; 424/435, 445, 447, 448; 514/945, 947

[56] References Cited

U.S. PATENT DOCUMENTS

| | | | |
|---|---|---|---|
| 3,053,255 | 9/1962 | Myer | 604/307 |
| 3,339,546 | 9/1967 | Chen . | |
| 3,972,328 | 8/1976 | Chen . | |
| 4,060,081 | 11/1977 | Yannas et al. | 128/156 |
| 4,292,972 | 10/1981 | Pawelchak et al. . | |
| 4,320,753 | 3/1982 | Lenz et al. | 128/156 |
| 4,367,732 | 1/1983 | Poulsen et al. | 128/156 |
| 4,393,080 | 7/1983 | Pawelchak et al. . | |
| 4,538,603 | 9/1985 | Pawelchak et al. | 128/156 |
| 4,592,753 | 6/1986 | Panoz | 604/897 |
| 4,655,766 | 4/1987 | Theeuwes et al. | 604/896 |
| 4,699,146 | 10/1987 | Siverding | 126/640 |
| 4,711,780 | 12/1987 | Fahim | 424/145 |
| 4,717,378 | 1/1988 | Perrault et al. | 604/20 |
| 4,728,642 | 3/1988 | Pawelchak et al. | 514/57 |
| 4,743,499 | 5/1988 | Volke | 128/156 |
| 4,747,401 | 5/1988 | Potter et al. | 128/156 |

FOREIGN PATENT DOCUMENTS 0190814 8/1986 European Pat. Off. .

OTHER PUBLICATIONS

Healing Wounds: Occlusion or Exposure, Oscar M. Alvarez, Ph.D, John M. Hefton, Ph.D, William H. Eaglstein, M.D., Infections in Surgery, Mar. 1984, pp. 173–181.

Primary Examiner—C. Fred Rosenbaum
Assistant Examiner—Mark O. Polutta
Attorney, Agent, or Firm—Brumbaugh, Graves, Donohue & Raymond

[57] ABSTRACT

The invention provides a method of treating wounds in accordance with stages in the healing process by providing environments ideally suited to each stage of chronic wound repair. These environments are designed to improve cell and enzyme function. In the first phase of the treatment, the wound is treated with a debridement dressing which creates an acidic, hypoxic, warm and airtight environment. The debridement dressing comprises a hydrocolloid adhesive combination containing from about 35% to 50% pectin or other hydrocolloid or hydrophilic particle capable of reducing the pH, and further includes a means for monitoring the pH at the wound/dressing interface without removing the dressing.

The second phase of the wound treatment is designed to enhance regeneration and provide natural protection against pathogenic invasion. The regeneration dressing used in this phase of treatment comprises a hydrocolloid adhesive containing 5% to 10% pectin to provide wet tack and 30% to 60% of a highly absorptive hydrocolloid or hydrophilic material such as sodium carboxymethylcellulose.

The regenerative phase of the treatment yields a healed but fragile wound with thin epidermis which is prone to reinjury. Accordingly, the final phase of the treatment involves a protective dressing which promotes thickening of the epidermal cells, thus strengthening the healed wound. The protective dressing for use in this third phase contains 0.05% to 20% hyaluronic acid, preferably in a carrier or absorbent which will provide controlled delivery over a period of 24 to 96 hours.

16 Claims, 2 Drawing Sheets

THREE STEP WOUND TREATMENT METHOD AND DRESSING THEREFOR

BACKGROUND OF THE INVENTION

This present invention relates to improved hydrocolloid/hydrophilic powder-containing wound dressings and to a three-dressing treatment regime for chronic wounds.

The use of hydrocolloids in bandages has been described in U.S. Pat. Nos. 3,339,546 to Chen; 4,538,603 to Pawelchak et al.; 4,393,080 to Pawelchak et al.; 3,972,328 to Chen; and 4,292,972 to Pawelchak et al. Each of these patents describes the use of a hydrocolloid-containing adhesive material in the construction of wound dressings. The disclosed purpose of the hydrocolloid is to provide wet-tack to the adhesive material, thus making it suitable for adhesion to moist surfaces.

While these dressings provided an initial approach to the treatment of moist or exudative wounds, several drawbacks to their use have become apparent. In particular, during the initial stages of healing in chronic wounds, i.e. debridement, or in highly exudative acute wounds leakage of wound fluid from the edges of the dressing, e.g. strike-through, is a significant problem. This results in the breaking of the barrier increasing the chances of bacterial infection, as well as in a messy, difficult to remove adhesive exudate. Furthermore, it has been found that these previously known dressings are not ideal for use throughout the healing process since the environments created thereby do not optimize certain processes critical to repair such as debridement, granulation and protection after the wound is healed. Moreover, these dressings can have detrimental effects if left on for too long a period of time as a result of hair growing into the sticky hydrocolloid/adhesive mass. In these circumstances, removal of the dressing can be painful and result in reinjury to the newly healed wound.

It is an object of this invention to provide a series of wound dressings adapted for use in a novel three-step wound treatment regimen that overcomes these disadvantages.

SUMMARY OF THE INVENTION

The invention provides a method of treating wounds in accordance with stages in the healing process by providing environments ideally suited to each stage of chronic wound repair. These environments are designed to improve cell and enzyme function. In the first phase of the treatment, the wound is treated with a debridement dressing which creates an acidic, hypoxic, warm and airtight environment. The debridement dressing comprises a hydrocolloid adhesive combination containing from about 35% to 50% pectin or other hydrocolloid or hydrophilic particle capable of reducing the pH, and further includes a means for monitoring the pH at the wound/dressing interface without removing the dressing. When the pH has decreased to between 4.8 and 6.5 due to the natural activity of the pectin, or other acidic component, the environment for autolytic debridement is established. The debridement dressing should be left in place for 24-48 hours. After this period of time, the pH increases again, allowing the pH monitoring means to provide an indication of when the debridement dressing should be removed.

The second phase of the wound treatment is designed to enhance regeneration and provide natural protection against pathogenic invasion. The regeneration dressing used in this phase of treatment comprises a hydrocolloid adhesive containing 5% to 10% pectin to provide wet tack and 30% to 60% of a highly absorptive hydrocolloid or hydrophilic material such as sodium carboxymethylcellulose, starch acrylonitrile, maleic anhydride copolymers, etc. The higher absorption rate of the absorptive material is significant in displacing wound fluid exudate, thus preventing dressing strike-through. The dressing may advantageously include a pH indicator means.

The environment created in the second phase of treatment is approximately neutral (pH 6.5–7.5), slightly hypoxic, warm and moist. In addition, the spongy gel-like mass created by the swelling of the hydrocolloid/adhesive creates an environment which prolongs the life span of certain blood-borne cells, such as monocytes and neutrophils, which perform functions critical to infection protection and further healing.

The regenerative phase of the treatment yields a healed but fragile wound with thin epidermis which is prone to reinjury. Accordingly, the final phase of the treatment involves a protective dressing which promotes thickening of the epidermis, thus strengthening the healed wound. The protective dressing for use in this third phase contains 0.05% to 20% hyaluronic acid, preferably in a carrier or absorbent which will provide controlled delivery over a period of 24 to 96 hours.

DETAILED DESCRIPTION OF THE INVENTION

Treatment of wounds in accordance with the invention involves utilization of three successive dressing types adapted to enhance the overall healing process by providing specific biological environments to facilitate the phases of chronic wound healing. The three dressing types act to promote debridement, regeneration and tissue strength, respectively.

Phase I-Debridement

Figure 1A:
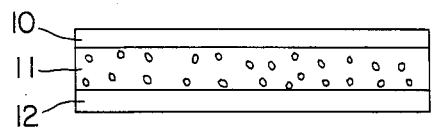
FIG. 1(a) shows a cross-section of an embodiment of a debridement promoting dressing according to the invention.
Figure 1B:
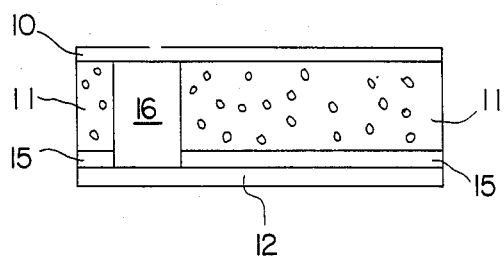
FIG. 1(b) shows a second embodiment of a debridement promoting dressing according to the invention.

The first phase of the treatment regimen according to the invention involves application of a dressing particularly adapted to promote wound debridement by creating an acidic, hypoxic environment. Such an environment can be created using debridement promoting hydrocolloid-containing dressings such as those shown in FIG. 1(a) and (b). Looking to FIG. 1(a), one embodiment of a debridement dressing comprises a layer of an occlusive film 10, a layer of foam 11, and a layer of a hydrocolloid-containing adhesive 13. A second embodiment of a debridement dressing according to the invention, shown in FIG. 1(b), comprises an occlusive film 10, a layer of foam 11, a tie layer 15, a layer of hydrocolloid-containing adhesive 12, and a pH indicator region 16. A pH indicator region can also be advantageously incorporated in the wound dressing depicted in FIG. 1(a).

The hydrocolloid-containing adhesive layer 13 in the debridement dressing according to the invention contains a hydrocolloid or hydrophilic material or acidic buffering agent capable to reducing the pH at the wound/dressing interface to between 4.8 and 6.5, an absorbent material such as carboxymethylcellulose, and polyisobutylene (Vistanex ®). Pectin, and particularly citrus pectin, is the preferred hydrocolloid for use in debridement promoting dressings according to the invention, although carrageenan and alginates can also be used.

Table I shows the relationship between pectin concentration and the pH of the wound fluid after 24 hours. From this data, it is clear that pectin concentrations from about 35% to about 50% are preferred to achieve the pH which is essential to optimum debridement. Lower levels of pectin do not lower the pH sufficiently to promote debridement, while higher levels create the risk of burning due to high acidity.

In addition to pectin, the adhesive layer of the debridement dressing contains 5% to 20% carboxymethylcellulose, and 30 to 50% polyisobutylene. The layer may also contain a plasticizer such as mineral oil, and starch acrylonitrile for pliability and increased absorption. Advantageously, cotton linters or similar fibrous materials are incorporated into the adhesive layer to stabilize the layer against flow and to improve absorptive properties Over the adhesive layer is disposed a foam layer 11 and an occlusive film layer 10 which provide an area for fluid displacement, insulation to maintain a warm environment padding, a protective barrier, and added dimensional stability to the dressing. The foam 11 can be joined to the adhesive layer 12 using a tie layer 15 such as that disclosed in U.S. Pat. No. 4,538,603 of Pawelchak et al., which is incorporated herein by reference, It is possible to utilize fully reticulated, i.e., 100% open cell foam, which has desirable properties from the viewpoint of fluid reservoir capacity handling, packaging and storage.

The occlusive films for use in the debridement promoting dressing can be made from any suitable material providing a water proof barrier. Suitable materials include polyurethane, copolyester, polyvinylidene chloride, polyvinyl alcohol, and polyethylene. It is not necessary for the film to be oxygen impermeable, since the adhesive layer provides the hypoxic environment. The complete dressing should preferably, however, provide an environment in which $pO_2$ is from 7–14 mm Hg. The film, can be perforated if desired.

The debridement promoting dressing should be removed after 24 to 72 hours, or when the pH at the wound/dressing interface has passed out of the safety range between pH 4.8 and 6.5. To facilitate removal at the correct time, the debridement promoting dressing according to the invention advantageously includes a means for monitoring the pH of the wound fluid. While this means could be simply a means for removing wound fluid for remote pH testing, it is preferably an integrated indicator strip which, for example, changes color to signal that the desired pH as been reached or to indicate that the pH is within the designated safety range.

EXAMPLE 1

Three different formulations of the adhesive layer for the debridement dressing are prepared as follows:

|  | Formulation | | |
| --- | --- | --- | --- |
|  | I | II | III |
| Pectin | 43% | 38% | 49% |
| Carboxymethylcellulose | 7% | 12% | 11.5% |
| Mineral Oil | 2% | 1% | 0.5% |
| Cotton Linters | 8% | 6% | — |
| Vistanex ® | 40% | 40% | 40% |
| Starch Acrylonitrile | — | 3% | — |

Each of these formulations is effective in promoting wound debridement.

EXAMPLE 2

The effectiveness of various pectin containing formulations as debridement dressings was evaluated by in vitro testing of eschar strips. The strips were excised from full thickness, third degree chemical burns, 24 hours after burning, and placed in contact with the various formulations for 24 hours. At the end of that time, strips from each treatment regimen were tested for tensile strength, a reduced tensile strength being indicative of eschar breakdown and wound debridement.

The formulations tested and the tensile strength results obtained are summarized in Table II. From these results, it can be seen that adhesives containing about 40% or more pectin are preferred to achieve optimum debridement. Indeed, formulations containing 35% pectin exhibit a markedly lesser effect than those containing 40% pectin.

The debridement dressing described above can be used as part of a three phase wound treatment regimen leading to a healed wound. It can also be used alone, for example to prepare a wound bed for receiving a surgical graft.

Phase II-Regeneration

Following wound debridement, the debridement promoting dressing is removed, and a second dressing adapted to promote tissue regeneration is applied. Structurally, this regeneration promoting dressing can be essentially identical to the debridement promoting dressing. The desired environment for regeneration is approximately neutral, however, and thus the formulation of the adhesive layer is different.

The adhesive layer of the regeneration promoting dressing comprises an amount of pectin or other hydrocolloid sufficient to provide wet tack, but which does not substantially lower the pH of the wound fluid; an increased amount of a highly absorptive material such as carboxymethylcellulose or starch acrylonitrile and polyisobutylene (Vistanex ®). In addition, the adhesive layer can include a plasticizer such as mineral oil, and cotton linters to stabilize the adhesive layer.

The adhesive layer in the regeneration promoting dressing may be located only around the edges of the dressing but the advantageous prolongation of PMN and macrophage lifetimes may be lost or reduced if large amounts of the adhesive layer are omitted. Therefore, the preferred dressing includes a substantially continuous layer of adhesive.

EXAMPLE 3

Three different formulations of the adhesive layer for the regeneration promoting dressing are prepared as follows:

|  | Formulation | | |
| --- | --- | --- | --- |
|  | IV | V | VI |
| Pectin | 20 | 18 | 25 |
| CMC | 30 | 25 | 25 |
| Mineral Oil | 5 | 2 | 3 |
| Cotton Linters | 8 | 10 | 7 |
| Vistanex ® | 40 | 45 | 40 |

Each of the formulations is effective in promoting regeneration.

The regeneration promoting dressing is generally left on for a period of 1 to 15 days, during which time the wound may exude large quantities of fluid. Because of this, the inclusion of increased levels of carboxymethylcellulose and cotton linters are particularly important to the prevention of strike-through of wound fluid and undesirable flow of this fluid away from the wound dressing.

Figure 2:
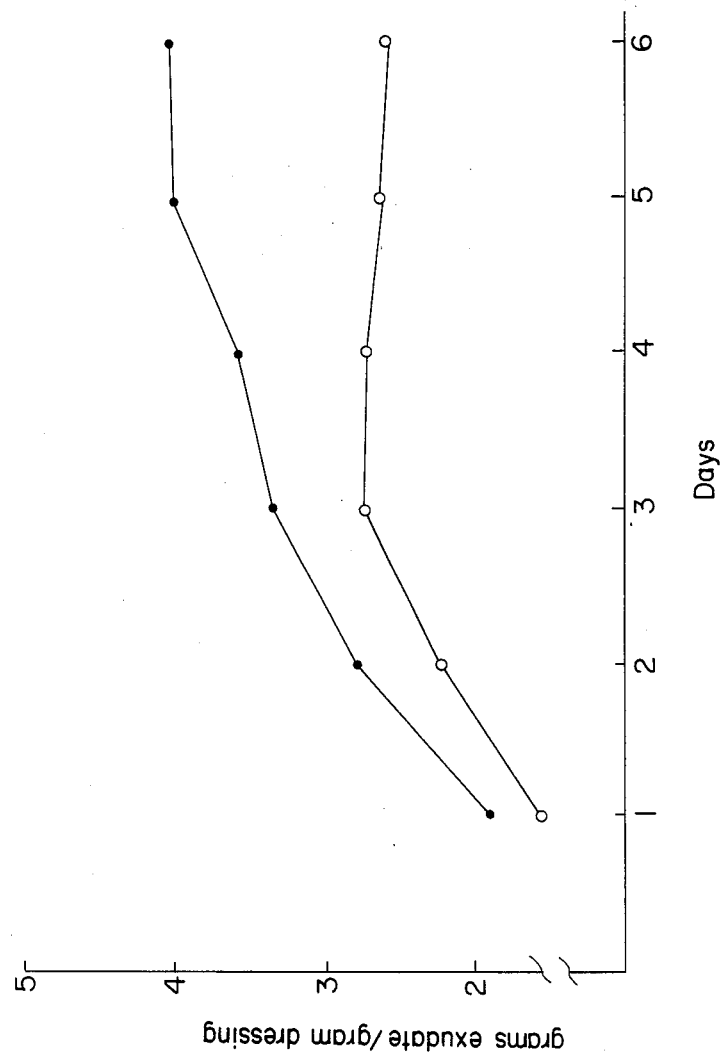
FIG. 2 graphically compares the adsorption of fluids by sodium carboxymethylcellulose and gelatin in pectin containing formulations.

FIG. 2 shows graphically the differing abilities of carboxymethylcellulose and gelatin to absorb fluids as a function of time. In FIG. 2, line 1 shows absorption of simulated wound exudate by a hydrocolloid formulation containing pectin (20 parts), sodium carboxymethylcellulose (30 parts), mineral oil (5 parts), cotton linters (8 parts) and Vistanex ® (40 parts). For comparison, line 2 shows absorption for a comparable formulation in which 30 parts gelatin is substituted for the sodium carboxymethylcellulose. From this figure it is clear that both the ultimate absorptive capacity and the rate of fluid uptake is superior using sodium carboxymethylcellulose. Because of this, the chance of fluid build-up sufficient to cause strike-through is substantially reduced in the regeneration promoting dressings according to the invention which contain higher levels of carboxymethylcellulose.

The inclusion of cotton linters in the adhesive layer reduces the ability of the layer to flow. Because of this, wound fluid/adhesive mixtures are less likely to flow away from the dressing and into contact with clothing, hair, or bedding. This is important because of the substantial difficulties which are encountered in attempting to remove polyisobutylene from such materials.

Phase III-Epidermal Thickening

After 7 to 30 days depending on the wound, tissue regeneration is essentially complete, but the newly healed area remains more fragile than the surrounding skin and is prone to reinjury. It is possible to merely provide a protective covering for the wound during this stage of the healing process. According to the invention, however, it is preferred to provide a third wound dressing which is adapted to promote epidermal thickening and thereby reduce the risk of reinjury.

Epidermal thickening can be promoted by treating the partially healed wound with hyaluronic acid. Hyaluronic acid can advantageously be applied in an ointment base preferably at a concentration of 0.05% to 20%. The wound can then be left uncovered, but is preferably covered with an occlusive film to provide further protection and enhanced penetration during the epidermal thickening process.

The third dressing according to the invention comprises a pad of a matrix material saturated with hyaluronic acid affixed to an occlusive film. The film is $H_2O$-impermeable but is oxygen and moisture vapor permeable. In particular the film should have an oxygen permeability of about 120 to 800 $cm^3$/100 $in^2$/ml/24 h/atm and a moisture vapor transmission rate of about 300 to 2000 $g/cm^2$/24 h at 37° C. and 100%–10% relative humidity. Suitable materials include microporous films of copolymer ester and polyurethane. The film, or the pad have a layer of adhesive for affixing the dressing to the skin. The matrix material can be a woven or nonwoven fabric such as gauze, a foam, or a cross-linked polymeric gel and provides dimensional stability and a measure of controlled delivery of the hyaluronic acid to the wound surface.

EXAMPLE 4

Three formulations of hyaluronic acid containing ointments are made as follows:

|  | Formulation | | |
| --- | --- | --- | --- |
|  | VII | VIII | IX |
| Hyaluronic Acid | 1% | 0.05% | 0.75% |
| Carbomer 940 | 80% | 80% | 80% |
| Polyethyleneglycol | 21% | 21.5% | 21.25% |

Each formulation is effective for promoting epidermal thickening.

EXAMPLE 5

The effectiveness of a number of hyaluronic acid concentrations as promoters of epidermal thickening was evaluated. Five ointments containing 0.05–10% hyaluronic acid were prepared in a base of hydrophilic ointment (Aquaphor ®). These ointments were applied, along with the base alone as a control to the skin of domestic pigs. Epidermal thickening was determined by measuring the thickness of the epidermis at 400X magnification.

The results of these tests are shown in Table III. All levels of hyaluronic acid tested showed a substantial improvement in epidermal thickness. Microscopic evaluation reveals that thickening is the result of larger, plumper cells, as opposed to an increase in the number of cells.

While the discussion hereinabove focuses on the preferred and advantageous use of the three dressings in combination, it is also a part of the invention to use each of the dressings individually in the treatment of appropriate wounds in conjunction with other healing techniques.

TABLE I

| EFFECT OF CITRUS PECTIN ON WOUND FLUID pH | |
| --- | --- |
| PECTIN CONCENTRATION (%) | WOUND FLUID pH |
| 10[a] | 7.1 ± 0.2 |
| 15 | 7.0 ± 0.2 |
| 20 | 6.8 ± 0.15 |
| 25 | 6.6 ± 0.2 |
| 30 | 6.5 ± 0.2 |
| 35 | 5.5 ± 0.12 |
| 40 | 5.3 ± 0.11 |
| 45 | 5.0 ± 0.15 |
| 50 | 4.7 ± 0.1 |
| 55 | 4.5 ± 0.1 |
| 60 | 4.5 ± 0.2 |
| 80 | 4.0 ± 0.2 |
| 100 | 4.1 ± 0.1 |

[a]Percent of total adhesive layer

TABLE II

EFFECT OF PECTIN ON ESCHAR BREAKDOWN IN VITRO

| PECTIN CONCENTRATION* | FORMULATION | ESCAR STRIP | TENSILE STRENGTH |
|---|---|---|---|
| 20 | a | 4.28 | 0.36 |
| 25 | b | 4.75 | 0.21 |
| 30 | c | 3.97 | 0.2 |
| 35 | d | 3.08 | 0.2 |
| 40 | e | 1.25 | 0.15 |
| 45 | f | 1.03 | 0.05 |
| 50 | g | 1.11 | 0.10 |
| 55 | h | 0.95 | 0.15 |
| 60 | i | 0.99 | 0.2 |
| 65 | j | 0.89 | 0.15 |
| 80 | k | 0.65 | 0.11 |
| 100 |  | 0.60 | 0.25 |

*% of total adhesive mass

| Formulation | PECTIN | CMC | GELATIN | POLYISOBUTYLENE |
|---|---|---|---|---|
| a | 20 | 20 | 10 | 50 Vistanex ® |
| b | 25 | 20 | 10 | 45 |
| c | 30 | 20 | 10 | 40 |
| d | 35 | 20 | 10 | 35 |
| e | 40 | 20 | 10 | 30 |
| f | 45 | 20 | 10 | 25 |
| g | 50 | 20 | 10 | 20 |
| h | 55 | 20 | 10 | 20 |
| i | 60 | 20 | 10 | 10 |
| j | 65 | 20 | 5 | 10 |
| k | 80 | 5 | 5 | 10 |

TABLE III

EFFECT OF HYLAURONIC ACID CONTAINING GEL ON EPIDERAL THICKENING

| % H.A. | EPIDERMAL THICKENING |
|---|---|
| 1 | 8.5 ± 0.3 |
| 2 | 8.0 ± 0.3 |
| 3 | 8.5 ± 0.2 |
| 5 | 9.5 ± 0.3 |
| 10 | 8.2 ± 0.5 |
| 0 | 5.5 ± 0.2 |

<sup>a</sup>Measured at the rete peg region (longest) 1 mm grids at 400x magnification.

I claim:

1. A wound dressing which enhances debridement comprising:
   (a) an adhesive layer suitable for direct application to a wound comprising polyisobutylene and a hydrophilic hydrocolloid material capable of reducing the pH at the wound/dressing interface to between 4.8 and 6.5; and
   (b) means for monitoring the pH at the wound dressing interface, wherein the dressing is adapted to provide a hypoxic and acidic environment for the wound.

2. A wound dressing according to claim 1, further comprising a layer of a water impermeable film disposed on one surface of the adhesive layer.

3. A wound dressing according to claim 2, further comprising a layer of foam situated between the adhesive layer and the water-impermeable layer.

4. A wound dressing according to claim 3, wherein the foam is 100% open cell foam, and further comprising a second film layer disposed between the foam layer and the adhesive layer.

5. A wound dressing according to claim 1, wherein the hydrocolloid material is selected from the group consisting of pectin, carrageenan, and alginates.

6. A wound dressing according to claim 5, wherein the hydrocolloid is pectin.

7. A wound dressing according to claim 6, wherein the pectin is derived from citrus fruits.

8. A wound dressing according to claim 6, wherein the pectin is treated with an acidic buffer to provide a lower pH environment.

9. A wound dressing according to claim 1, wherein the means for monitoring the pH at the wound/dressing interface is an indicator region visible on the exterior surface of the dressing that indicates when the pH at the wound/dressing interface is between 4.8 to 6.5.

10. A dressing according to claim 6, wherein the adhesive layer comprises 35–50% pectin.

11. A method for treating wounds in need of debridement comprising:
    (a) covering a wound with a debridement promoting dressing which creates a moist hypoxic environment, wherein the dressing causes a gradual decrease in the pH to 5.3 or under at the wound/dressing interface; and
    (b) removing the debridement dressing when the pH at the wound/dressing interface reaches a pH outside of the range from 4.8 to 6.5.

12. A method according to claim 11, further comprising the step of covering the debrided wound with a regeneration promoting dressing that creates a moist hypoxic environment having a pH of 6.5 to 7.5.

13. A method according to claim 12, further comprising the steps of
    removing the regenerative dressing when cell regeneration is substantially complete as indicated by a change in pH outside the range of 6.5 to 7.5, and
    applying a protective dressing to the regenerated wound, said protective dressing comprising hyaluronic acid in an amount effective to promote epithelial thickening.

14. A method according to claim 11, wherein the debridement promoting dressing comprises an adhesive layer comprising 35% to 50% pectin, carboxymethylcellulose, and polyisobutylene, said adhesive layer acting to lower the pH at the wound/dressing interface.

15. A method according to claim 12, wherein the regeneration promoting dressing comprises an adhesive layer comprising 5% to 20% pectin, 20% to 40% carboxymethylcellulose, and polyisobutylene.

16. A method for treating debrided wounds comprising the steps of
    covering the debrided wound with a regeneration promoting dressing the creates a moist hypoxic environment having a pH of 6.5 to 7.5,
    removing the regenerated dressing when call regeneration is substantially complete as indicated by a change in pH outside the range of 6.5 to 7.5, and
    applying a protective dressing to the regenerated wound, said protective dressing comprising hyaluronic acid in an amount effective to promote epithelial thickening.

* * * * *

UNITED STATES PATENT AND TRADEMARK OFFICE
CERTIFICATE OF CORRECTION

PATENT NO. : 4,813,942

DATED : March 21, 1989

INVENTOR(S) : Oscar M. Alvarez

It is certified that error appears in the above-identified patent and that said Letters Patent is hereby corrected as shown below:

Col. 3, line 62, "as" should read --has--;

Col. 7, line 33, "HYLAURONIC" should read --HYALURONIC--;

Col. 7, line 35, after "EPIDERMAL THICKENING" insert a superscript --a--;

Col. 8, line 55, "the" should read --that--;

Col. 8, line 57, "call" should read --cell--.

Signed and Sealed this

Thirteenth Day of August, 1991

Attest:

HARRY F. MANBECK, JR.

Attesting Officer

Commissioner of Patents and Trademarks